(12) United States Patent
Penichet et al.

(10) Patent No.: US 8,697,079 B2
(45) Date of Patent: Apr. 15, 2014

(54) IGE ANTIBODIES FOR THE TREATMENT OF CANCER

(75) Inventors: Manuel L. Penichet, Los Angeles, CA (US); Birgit C. Schultes, Arlington, MA (US); Christopher F. Nicodemus, Charlestown, MA (US); Tracy R. Daniels, Woodland Hills, CA (US); Gustavo Helguera, Long Beach, CA (US); Jose A. Rodriguez, Paramount, CA (US)

(73) Assignees: Quest Pharma Tech Inc., Alberta (CA); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/372,557

(22) Filed: Feb. 14, 2012

(65) Prior Publication Data

US 2013/0022614 A1 Jan. 24, 2013

Related U.S. Application Data

(63) Continuation of application No. 12/900,256, filed on Oct. 7, 2010, now abandoned, which is a continuation of application No. PCT/US2009/040085, filed on Apr. 9, 2009.

(60) Provisional application No. 61/043,682, filed on Apr. 9, 2008, provisional application No. 61/044,576, filed on Apr. 14, 2008, provisional application No. 61/159,069, filed on Mar. 10, 2009.

(51) Int. Cl.
*A61K 39/395* (2006.01)

(52) U.S. Cl.
USPC ............. 424/155.1; 424/134.1; 424/138.1; 424/139.1; 424/141.1; 424/805; 530/387.3; 530/387.7; 530/387.9; 530/388.8

(58) Field of Classification Search
None
See application file for complete search history.

(56) References Cited

U.S. PATENT DOCUMENTS 6,083,709 A * 7/2000 Reynolds et al. ............ 435/7.94
6,881,405 B2 * 4/2005 Leveugle et al. ........... 424/130.1

FOREIGN PATENT DOCUMENTS

WO  WO 9211031 A1 * 7/1992
WO  99/65523 A1 12/1999
WO  2008/091643 A2 7/2008

OTHER PUBLICATIONS

Romanov et al., Cancer Res. Mar. 15, 2004;64(6):2083-9.*
Sinha et al., Prostate. Nov. 1, 2001;49(3):172-84.*
MacGlashan et al., J Immunol. Dec. 1985;135(6):4129-34.*
Daniel-Wells et al., BMC Cancer. Apr. 17, 2013;13:195. doi: 10.1186/1471-2407-13-195.*
Karagiannis, S. N., et al., "Activity of human monocytes in IgE antibody-dependent surveillance and killing of ovarian tumor cells," European Journal of Immunology, 33(4): 1030-1040 (2003).
Karagiannis, S. N., et al., "Role of IgE receptors in IgE antibody-dependent cytotoxicity and phagocytosis of ovarian tumor cells by human monocytic cells," Cancer Immunology Immunotherapy, 57(2): 247-263 (2007).
Panagiotis Karagiannis et al., "Characterisation of an engineered trastuzumab IgE antibody and effector cell mechanisms targeting HER2/neu-positive tumour cells", Cancer Immunology, Immunotherapy, 58 (6):915-930 (2008).
Daniels T. R., et al., "Novel antibodies for prostate cancer therapy", Proceedings of the American Association for Cancer Research Annual Meeting, 100th Annual Meeting of the American-Association-For-Cancer-Research; Denver, CA, USA; 50:416, Apr. 18-22, 2009.
Daniels T. R., et al., "Monoclonal IgE Targeting Prostate Specific Antigen (PSA) or HER2/NEU (HER2) as a Tumor Specific Immunotherapeutic Strategy," Journal of Immunotherapy, 25th Annual Scientific Meeting of the International Society for Biological Therapy of Cancer; Washington, DC, USA; Sep. 30-Oct. 4, 2010, 33(8):894-895 (2010).
Daniels, T. R., et al., "Targeting HER2/with a fully human IgE to harness the allergic reaction against cancer cells," Cancer Immunology Immunotherapy, 61(7):991-1003, Nov. 30, 2011.
Campbell, I. G., et al., "Folate-binding Protein is a Marker for Ovarian Cancer," Cancer Research, American Association for Cancer Research, 51:5328-5338 (1991).
Nagy, E., et al., "Growth inhibition of murine mammary carcinoma by monoclonal IgE antibodies specific for the mammary tumor virus," Cancer Immunology, Immunotherapy CII, 34(1):63-69 (1991).

* cited by examiner

*Primary Examiner* — Michael Szperka
(74) *Attorney, Agent, or Firm* — Elmore Patent Law Group, P.C.; Darlene A. Vanstone, Esq.; Carolyn S. Elmore, Esq.

(57) ABSTRACT

The present invention provides monoclonal IgE antibodies comprising Fc epsilon (ε) constant regions and variable regions comprising at least one antigen binding region specific for binding a single epitope of a circulating, tumor-associated antigen (TAA) that is not a cell surface antigen wherein the epitope of the targeted antigen is not highly repetitive or is a non-repetitive epitope. The IgE antibodies of the invention are useful in the treatment of cancer associated with the tumor antigen. In one embodiment the TAA is prostate-specific antigen (PSA).

18 Claims, 3 Drawing Sheets

IGE ANTIBODIES FOR THE TREATMENT OF CANCER

RELATED APPLICATIONS

This application is a continuation of U.S. application Ser. No. 12/900,256, filed Oct. 7, 2010, which is a continuation of International Application No. PCT/US2009/040085, which designated the United States and was filed on Apr. 9, 2009, published in English, which claims the benefit of U.S. Provisional Application Nos. 61/043,682, filed on Apr. 9, 2008, 61/044,576, filed on Apr. 14, 2008 and 61/159,069, filed on Mar. 10, 2009. The entire teachings of the above applications are incorporated herein by reference.

GOVERNMENT SUPPORT

This invention was made with government support under grant numbers CA107023, CA057152, and CA009120 awarded by the National Institutes of Health (NIH). The Government has certain rights in the invention.

BACKGROUND OF THE INVENTION

The newly arising field of AllergoOncology is based upon observations and studies showing that those individuals with raised levels of IgE (e.g. individuals who suffer from allergies) are much less likely to suffer from certain types of cancer. Researchers in this field are exploring the therapeutic potential of the IgE antibody class in the prevention and treatment of certain cancers, under the premise that redirected immune pathways developed as adaptive responses to microbial/parasitic infection might be directed against malignancy.

IgE antibodies mediate allergic and asthmatic reactions, characterized by immediate hypersensitivity, followed by an inflammatory delayed type response requiring the recruitment of effector cells. The uniqueness of the allergic reaction is due to the presence of mast cells and Langerhans/dendritic cells in the tissue that are sensitized by the IgE bound to the high-affinity FcεRI (Kinet, J P, *Annu. Rev. Immunol.*, 17: 931-72: 931-972 (1999); and Ravetch J V, and Kinet J P, *Annu. Rev. Immunol.*, 9: 457-492 (1991)). The activated Langerhans/dendritic cells migrate to local lymph nodes and stimulate cognate T cells, which migrate to the tissue, participate in the inflammatory response and stimulate antibody synthesis. IgE bound to mast cells and basophils can cause degranulation of the cells, but it requires cross-linking by the antigen the IgE recognizes. Following the acute phase of recruitment, eosinophils are recruited in the late-phase reaction. Activated eosinophils are strong mediators of antibody-dependent cell-mediated cytotoxicity (ADCC) via toxic granule proteins and cause tissue damage via pro-inflammatory cytokines and vasoactive lipid mediators (leukotrienes, prostaglandin D2, platelet-activating factor). The processing of the IgE containing immune complexes by Langerhans cells and dendritic cells is a critical step for the induction of the late-phase reaction. Activated T helper cells generate IL-4 and IL-5, which in turn recruits and activates eosinophils causing ADCC and antibody-dependent cell-mediated phagocytosis (ADCP) (Kinet, J P, *Annu. Rev. Immunol.*, 17:931-72.:931-972 (1999); Maurer, D., et al., *J. Immunol.*, 161: 2731-2739 (1998) and Maurer D., et al., *J. Immunol.*, 154: 6285-6290 (1995)).

While B cells can recognize antigen in its native conformation, T cells generally recognize antigen that has been "processed" by antigen presenting cells and then presented on the surface of the cell by major histocompatibility complex (MHC) molecules (Peakman, M. and Vergani, D., New York: Churchhill Livingston; (1997)). MHC molecules are receptors for peptide antigens. There are two classes of MHC molecules, termed MHC class I and MHC class II. Although united in their function of peptide antigen presentation and contact points for T cells, the differences in the structure and intracellular trafficking of the two types are critical because among other things, they elicit very different immune responses. A major obstacle in the creation of effective tumor immunity is that typically, there is poor presentation of tumor antigen on MHC class I and class II molecules together (cross-presentation). Dendritic cells are bone marrow-derived leukocytes that are more potent initiators of T cell-dependent immune responses than any other antigen presenting cells that have been tested (Peakman, M. and Vergani, D., New York: Churchill Livingston; (1997)). Unlike other antigen presenting cells, dendritic cells can acquire antigens from their environment and process them for cross-presentation, allowing activation of both $CD8^+$ and $CD4^+$ T cells. However, this process requires high antigen concentrations. Simultaneous presentation on MHC II provides for T helper cell activation. Depending on the stimuli, either production of cytokines IL-12 and IFN-γ by T helper (Th) cell 1 type and cytotoxic T lymphocytes (CTL) induction occurs (collectively referred to herein as the "Th1/Tc1 immune response") or IL-4, IL-5 and IL-10 is produced by Th2 cells for B cell help (referred to herein as "Th2 immune response"). An important factor in immune induction is the activation or maturation of the antigen presenting cells, which induces the expression of co-stimulatory molecules that are necessary to engage the T cell.

It is now believed that the engagement of the toll-like receptor (TLR) family (Okamoto, M. and Sato, M., *J. Med. Invest.*, 50: 9-24 (2003)) as well as other receptors including Fc receptors (Hamano, Y., et al., *J. Immunol.*, 164: 6113-6119 (2000) and Regnault, A., et al., *The Journal of Experimental Medicine*, 189: 371-380 (1999)) mediates activation and maturation of macrophages and dendritic cells, which is crucial for activating the innate immune system. Fc receptors have also been shown to facilitate antigen uptake and presentation. Researchers have shown that immune complex pulsed DC induce stronger $CD4^-$ and $CD8^+$ T cell responses as compared to DC pulsed with PSA alone (Berlyn, K A, et al., *Clin. Immunol.*, 101: 276-283 (2001)). Similarly, NY-ESO-1 as well as ovalbumin or pyruvate dehydrogenase are all presented to T cells much more efficiently when captured as an immune complexes rather than as free-antigen (Regnault A., et al., *The Journal of Experimental Medicine* 189:371-380 (1999); Nagata Y., et al., *Proc. Natl. Acad. Sci. U.S.A.*, 99: 10629-10634 (2002); Kita, H., et al., *J. Exp. Med.*, 195:113-123 (2002) and Schuurhuis, D H, et al., *J. Immunol.*, 168: 2240-2246 (2002)). The results suggest that effective cancer vaccines may be generated by administering antibodies that target circulating antigen and form immune complexes that target DC in vivo. The role of IgE as a component of an immune complex in altering antigen presentation is less understood and is believed to contribute to the aggravation and perpetuation of the atopic response to allergen as demonstrated in the IgE mediated influence enhancing Th2 (IL-4, IL-10) T cells responses to allergen. (Maurer et al, *JI* 161: 2731-2739, 1998). The art has not addressed non-atopic responses.

IgE binds to two types of Fc receptors, called FcεRI (or high-affinity FcεR) ($K_a=10^{11}$ $M^{-1}$) and FcεRII (or low-affinity FcεR, CD23) ($K_a<10^8$ $M^{-1}$). Therefore, unlike antibodies of the IgG class, IgE binds to its FcR with extremely high affinity which in the case of FcεRI is about three orders of magnitude higher than that of IgG for the FcRs (FcγRI-III) and in the case of FcεRII is as high as that of IgG for its high affinity FcγRI (Gould, H J, et al., *Annu. Rev. Immunol.*, 21: 579-628. Epub@2001 December@19.:579-628 (2003); Gounni, A S, et al., *Nature*, 367: 183-186 (1994); Kinet, J P, *Annu. Rev. Immunol.*, 17: 931-72:931-972 (1999) and Ravetch J V, and Kinet J P, *Annu. Rev. Immunol.*, 9: 457-492 (1991)). Because the IgE concentration in normal serum is usually very low (less than 1 μg/mL), the FcεR are typically available for occupancy if IgE is induced by allergies and parasitic infestation or if administered. The FcεRI is composed of four polypeptide chains, one α, one β, and two γ chains. The a chain contains the IgE binding site and is a member of the immunoglobulin supergene family. The FcεRII consists of one polypeptide chain which shows homology to animal lectin receptors. FcεRI is expressed on mast cells and basophils as well as Langerhans cells and dendritic cells where it is involved in antigen presentation, on eosinophils where it plays a role in defense against parasitic infection, and also on monocytes (see Kinet, J P, *Annu. Rev. Immunol.*, 17: 931-72.:931-972 (1999) for a review). Crosslinking of the FcεRI induces immediate release of mediators of inflammation such as histamine, leukotrienes, prostaglandin E2, or β-glucuronidase and delayed secretion of IL-4, 5, and 6. FcεRII is a member of the Ig superfamily, more widely expressed on resting and mature B cells, monocytes, follicular dendritic cells, macrophages, eosinophils, platelets, Langerhans cells, and a subset of T cells (10-15% of tonsillar T cells). IL-4 up-regulates FcεRII expression on B cells and macrophages. FcεRII on macrophages, eosinophils, and platelets mediates ADCC to schistosomules, enhance phagocytosis, and induce the release of granule enzymes (Gounni, A S, et al., *Nature*, 367: 183-186 (1994); Kinet, J P, *Annu. Rev. Immunol.*, 17: 931-72.:931-972 (1999) and Spiegelberg, H L., *J. Invest. Dermatol.*, 94: 49S-52S (1990)). FcεRII is involved in both IgE regulation and allergen presentation by B-cells, but understanding the functional roles of CD23 is further complicated by the fact that it exists both as a cell surface molecule and in a soluble form generated by cleavage from the cell surface; furthermore, it exists in both monomeric and oligomeric states (see Gould, H J, and Sutton, B J, *Nat. Rev. Immunol.*, 8: 205-217 (2008) for a review). CD23 responds to high levels of IgE by downregulating IgE secretion. In human monocytes, CD23 triggering results in release of pro-inflammatory cytokines including tumor necrosis factor (TNF)-α, IL-1, IL-6, and granulocyte/macrophage-colony stimulating factor (GM-CSF). IL-4 appears to play a central role in immediate-type hypersensitivity. It induces human B cells to secrete IgE and IgG4 and activated T helper cells. IL-4 also stimulates mast cell growth and up-regulates FcεRII expression.

Most of the antibodies used in the treatment of cancer, including FDA approved antibodies such as trastuzumab (HERCEPTIN®) and rituximab (RITUXAN®), are of the IgG class (Carter, P., IBC's Tenth International Conference. 6-9 Dec. 1999, La Jolla, Calif., USA. *IDrugs*, 3: 259-261 (2000); Carter, P., *Nat. Rev. Cancer*, 1: 118-129 (2001) and Carter, P J, *Nat. Rev. Immunol.*, 6: 343-357 (2006)). However, monoclonal IgE antibodies specific for tumor antigens have been reported. The application of IgE for the therapy of cancer was pioneered by Nagy et al. (Nagy, E., et al., *Cancer Immunol. Immunother.*, 34: 63-69 (1991)), who developed a murine IgE monoclonal antibody specific for the major envelope glycoprotein (gp36) of mouse mammary tumor virus (MMTV) and demonstrated significant anti-tumor activity in C3H/HeJ mice bearing a syngeneic MMTV-secreting mammary adenocarcinoma (H2712) (Nagy, E., et al., *Cancer Immunol. Immunother.*, 34: 63-69 (1991)). Kershaw et al. (Kershaw, M H, et al., *Oncol. Res.*, 10: 133-142 (1998)) developed a murine monoclonal IgE named 30.6, specific for an antigenic determinant expressed on the surface of colorectal adenocarcinoma cells. Mouse IgE 30.6 inhibited the growth of established human colorectal carcinoma COLO 205 cells growing subcutaneously in severe combined immune deficient (SCID) mice, although this effect was transient. By contrast, a mouse IgG 30.6 and a mouse/human chimeric IgE 30.6 did not show anti-tumor effects. The mouse IgE specific effect was attributed to the interaction of the antibody with FcεR bearing effector cells since the activity was specifically abrogated by prior administration of a non-specific mouse IgE (Kershaw, M H, et al., *Oncol. Res.*, 10: 133-142 (1998)). The lack of effect exhibited by the mouse/human chimeric IgE 30.6 is explained by the fact that mouse FcεRI binds mouse IgE, but not human IgE. Gould et al. (Gould, H J, et al., *Eur. J. Immunol.*, 29: 3527-3537 (1999)) developed a mouse/human chimeric IgE (MOv18-IgE) and IgG MOv18 (IgG1) specific for the ovarian cancer tumor-associated antigen folate binding protein (FBP). The protective activities of MOv18-IgE and MOv18-IgG1 were compared in a SCID mouse xenograft model of human ovarian carcinoma (IGROV1). Mice were reconstituted with human peripheral blood mononuclear cells (PBMC) to provide the model with effector cells capable of binding human IgE constant regions. The beneficial effects of MOv18-IgE were greater and of longer duration than those of MOv18-IgG1 demonstrating the superior anti-tumor effects of IgE antibodies (Gould, H J, et al., *Eur. J. Immunol.*, 29: 3527-3537 (1999)). In addition, the group of Gould et al. recently demonstrated for the first time monocyte-mediated IgE-dependent tumor cell killing by two distinct pathways, ADCC and phagocytosis (ADCP), mediated through FcεRI and FcεRII (Karagiannis, S N, et al., *Cancer Immunol. Immunother.*, 57: 247-263 (2008) and Karagiannis, S N, et al., *J. Immunol.*, 179: 2832-2843 (2007)). This group has also used this assay system to assess preliminary bioactivity of an anti-Her2 IgE construct, (Karragiannis P., *Cancer Immunol. and Immunother.* 2008 epub ahead of print). Since human PBMC are short-lived in SCID mice it is expected that the anti-tumor effect will be enhanced in humans where the supply of effector cells would be permanent. None of the studies could address the capacity of the mouse/human chimeric IgE to elicit an adaptive immune response due to the fact that murine APCs such as Dendritic cells do not express the FcεRI (Kinet, J P, *Annu. Rev. Immunol.*, 17: 931-72.:931-972 (1999)).

Relevant epidemiological studies on the association of allergic diseases with cancer support a lower risk of cancer among people with a history of allergies or high levels of serum IgE including different hematopoietic malignancies (Grulich, A E and Vajdic, C M, *Pathology*, 37: 409-419 (2005); Wang, H. and Diepgen, T L, *Allergy*, 60: 1098-1111 (2005); Grulich, A E, et al., *Cancer Epidemiol. Biomarkers Prev.*, 16: 405-408 (2007); Turner, M C, et al., *Am. J. Epidemiol.*, 162: 212-221 (2005); Wang, H. and Diepgen, T L, Br., *J. Dermatol.*, 154: 205-210 (2006); Wang, H., et al., *Int. J. Cancer*, 119: 695-701 (2006); Turner, M C, et al., *Int. J. Cancer*, 118: 3124-3132 (2006) and Melbye, M., et al., *J. Natl. Cancer Inst.*, 99: 158-166 (2007)) and solid tumors such as ovarian, colorectal, pancreatic cancer, and glioma (Wang, H. and Diepgen, T L, *Allergy*, 60: 1098-1111 (2005); Turner, M C, et al., *Am. J. Epidemiol.*, 162: 212-221 (2005); Wang, H., et al., *Int. J. Cancer*, 119: 695-701 (2006); Turner, M C, et al., *Int. J. Cancer*, 118: 3124-3132 (2006); Mills, P K, et al., *Am. J. Epidemiol.*, 136: 287-295 (1992); Wiemels, J L, et al., Cancer Res., 64: 8468-8473 (2004) and Wrensch, M., et al., Cancer Res., 66: 4531-4541 (2006)).

Furthermore, mice infested with nematodes are resistant to syngeneic mammary adenocarcinoma and show lower incidence of spontaneous mammary tumors (Ogilvie, B M, et al., Lancet., 1: 678-680 (1971) and Weatherly, N F, J. Parasitol., 56: 748-752 (1970)). Eosinophilia, either in peripheral blood or tumor-associated tissue, is frequently associated with some tumor types and also found after immunotherapy with IL-2, IL-4, GM-CSF, and antibody to CTLA-4 (Lotfi, R, et al., J. Immunother., 30: 16-28 (2007)). Within several tumor types including gastrointestinal tumors, this observation is associated with a significantly better prognosis, whereas their presence in rejecting allografts is largely seen as a harbinger of poor outcome (Lotfi, R. and Lotze, M T, J. Leukoc. Biol., 83: 456-460 (2008)). Matta et al. (Clin Cancer Res., 13:5348-5354 (2007)) have reported that multiple myeloma patients with relatively higher IgE levels had a better survival than patients with lower levels of IgE. Importantly, this is clearly reflected on the levels of IgE and not the other classes of immunoglobulins. These studies are consistent with a natural role of IgE in the immunosurveillance of cancer including multiple myeloma. Fu, et al. (Clin Exp Immunol, 153:401-409, 2008) demonstrated that antibodies of the IgE class isolated from pancreatic cancer patients mediate antibody-dependent cell-mediated cytotoxicity (ADCC) against cancer cells. Finally, treatment with omalizumab (XOLAIR®), which decreases free IgE in serum and down-regulates IgE receptors in effector cells to dampen IgE-mediated inflammatory response, appears to lead to a higher chance of developing cancer. Approximately 1 in 200 treated asthmatic patients developed breast, prostate, melanoma, non-melanoma skin, or parotid gland malignancies during the median observation period of 1 year while in the control group the incidence was 1 in 500 (Dodig, S., et al., Acta Pharm., 55: 123-138 (2005)). These studies suggest a natural role of IgE in the immunosurveillance of cancer with an estimated 186,320 new cases in the U.S. for 2008, prostate cancer is the most frequently diagnosed cancer (25% of all cancers) in men. Prostate cancer is the second leading cause of cancer deaths in American men, accounting for 10% (28,660 cases) of all cancer-related deaths. For reasons that remain unclear, incidence rates are significantly higher in African American men than in white men and death rates remain more than twice as high as those in white men (Jemal, A., et al., CA Cancer J. Clin., 58: 71-96 (2008); Cancer Facts & Figures. American Cancer Society (2008) and Cancer Facts and Figures for African Americans 2007-2008. American Cancer Society, 2008). According to the most recent data, the lifetime probability of developing prostate cancer is 1 in 6. Over the past 25 years, the 5-year survival rate for all stages combined has increased from 69% to almost 99% and relative 10-year and 15-year survival is 91% and 76%, respectively. The dramatic improvements in survival, particularly at 5 years, are mainly attributable to earlier diagnosis (Cancer Facts & Figures, American Cancer Society (2008)). As a result of the high survival rates, many patients die "with" their disease rather than "from" their disease, albeit following years of invasive therapies.

The high frequency of intercurrent mortality as opposed to prostate cancer-specific mortality, and the morbidity of currently available treatments for asymptomatic individuals, has led some groups to propose a less interventional or deferred-therapy approach for early-stage disease (Cancer Facts & Figures, American Cancer Society (2008)). More controversial is the management of tumors with adverse features such as a positive margin, vascular invasion, or capsular penetration. Most urologists and radiation oncologists, however, do not recommend additional therapy if the PSA is undetectable. If PSA persists, and depending on the findings at surgery, the probability that the patient has subclinical micrometastatic disease is high (DeVita, V T, et al., Cancer—principles and practice of oncology (1997)). Clearly there is a need for an effective, yet relatively benign treatment for men with possible minimum disease (i.e., an effective cancer vaccine or immunotherapy). For patients with metastatic disease or persistence of PSA, which account for approximately 15% of patients (Cancer Facts & Figures, American Cancer Society (2008)), androgen ablation through surgical or pharmaceutical approaches often controls malignancy for extended periods; however, adverse effects are significant, and ultimately, prostate cancer becomes hormone refractory. Chemotherapy and palliative radiotherapies can help with patient management, but cannot cure this condition.

Prostate cancer is associated with two well characterized and highly specific antigens, prostate-specific antigen (PSA) and prostate-specific membrane antigen (PSMA). PSA is a particularly attractive target antigen for immunotherapy because this 33-kDa protein (serine protease) is almost exclusively synthesized within the prostate gland and found circulating in human serum. PSA can also be identified in the cytoplasmic compartment of prostate epithelium and prostate tumor cells and is released into the tumor microenvironment. The increasing serum levels of PSA associated with the development of prostate cancer make it both a useful marker for disease progression as well as a promising target for immunotherapy, particularly T cell mediated immunotherapy (Zhang, S., et al., Clin. Cancer Res., 4: 295-302 (1998)). High levels of PSA are found in the tumor (Katzenwadel, A. et al., Anticancer Res., 20: 1551-1555 (2000); Sinha, A A, et al., Anticancer Res., 19: 893-902 (1999); Sinha, A A, et al., Anat. Rec., 245: 652-661 (1996) and Mirochnik, Y., et al., Drug Deliv., 11: 161-167 (2004)). Vaccination in both humans (Roos, A K, et al., Prostate, 62: 217-223 (2005) and mice (Pavlenko, M., et al., Br. J. Cancer, 91: 688-694 (2004)) with DNA encoding PSA has demonstrated specific immunity as measured by PSA-specific cytotoxic T lymphocytes (CTLs). In addition, this approach was protective when mice were challenged with PSA-expressing tumors. Additionally, in a phase II clinical trial investigating the immunogenicity of autologous DC pulsed with human recombinant PSA, specific immunity was generated in several patients as demonstrated by the presence of PSA-specific T cells detected by enzyme-linked immunoSPOT (ELISPOT) (Barrou, B., et al., Cancer Immunol. Immunother., 53: 453-460 (2004)).

Given the profound medical impact of prostate cancer (28,660 expected deaths from prostate cancer for 2008), the relatively high mortality rate for African American men, and the lack of adequate therapies for men with refractory metastatic disease, there is a need to develop innovative modalities of treatment in this indication.

SUMMARY OF THE INVENTION

The present invention provides therapeutic monoclonal IgE antibodies comprising Fcε constant regions and variable regions comprising at least one antigen binding region specific for binding a single epitope of a circulating, tumor-associated antigen (TAA) that is not a cell surface antigen wherein the epitope of the targeted antigen is not highly repetitive or is a non-repetitive epitope. The IgE antibodies of the invention are capable of mediating an ADCC immune response, a Th1/Tc1 type immune response, or both, when administered to a subject capable of mounting such an immune response. Also provided are methods of inducing IgE-mediated immune responses against circulating TAA antigens that are not cell surface antigens for use in inhibiting or killing tumors secreting the target antigens.

DETAILED DESCRIPTION OF THE INVENTION

Figure 1:
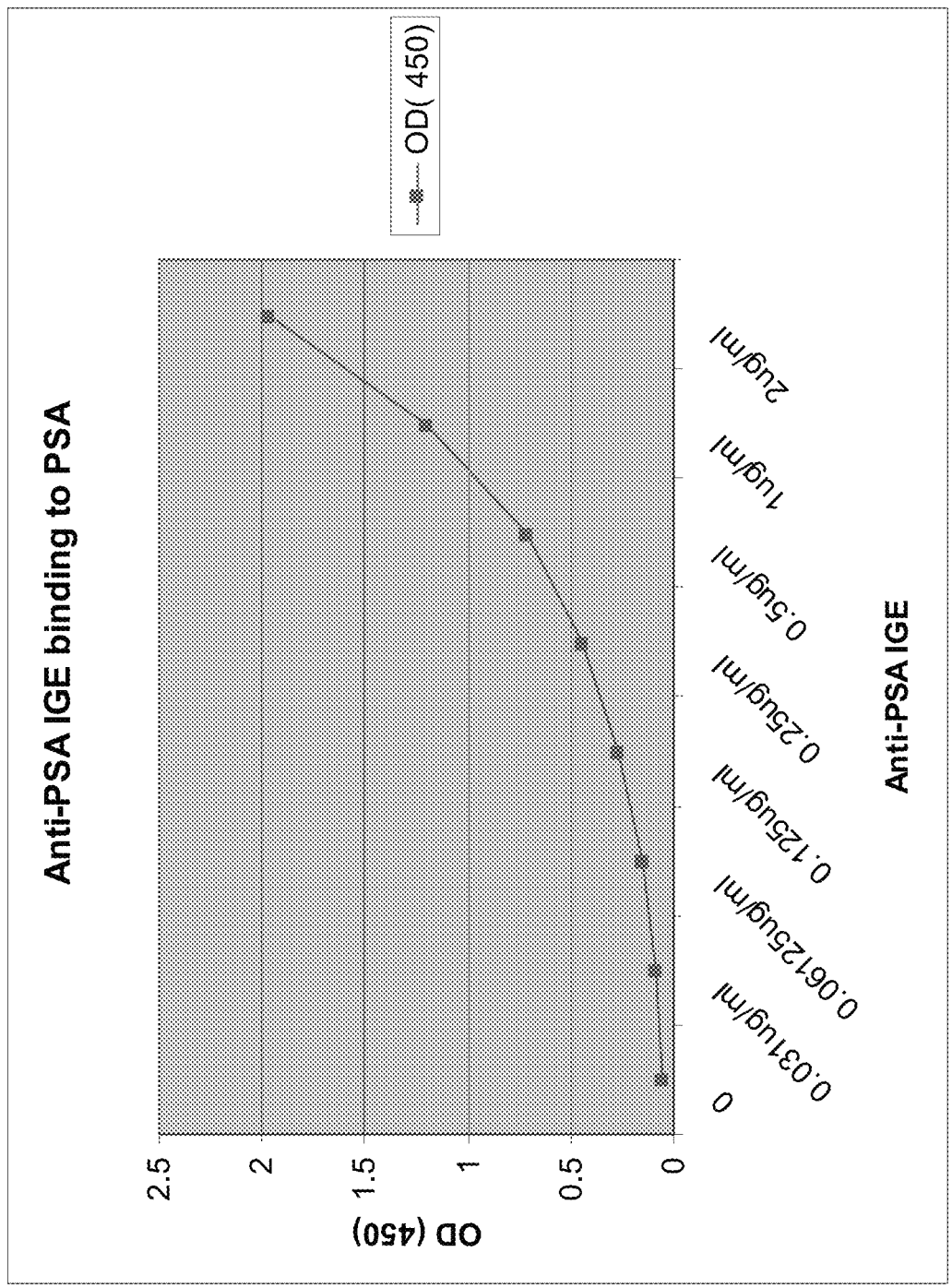
FIG. 1: IgE ELISA of purified antibody. Microwell Maxi-Sorp plates are coated with PSA (1.5 ug/ml in PBS) and incubated at 4° C. overnight. After washing plates are blocked with 3% BSA/PBS for 30-60 minutes at RT. Samples containing anti-PSA IgE are added in serial dilutions (2 ug/ml, 1 ug/ml, 0.5 ug/ml, 0.25 ug/ml 0.125 ug/ml 0.0625 ug/ml, 0.31 ug/ml) and incubated for 2 hr at RT. The presence of anti-PSA specific IgE Abs is detected by biotinylated goat anti-Human IgE (1:2000 dilution, KPL) followed by Strepavidin-HRP (1:10,000) added separately and incubated for 30-60 min each. The assay is developed with TMB and the reaction is terminated with stop solution ($H_2SO_4$). Absorbance is measured at 405 nm.

The present invention provides novel IgE antibodies to direct hypersensitivity reactions and alter antigen processing to cancer while avoiding systemic hypersensitivity reactions (e.g. systemic anaphylaxis). The present invention provides novel IgE monoclonal antibodies capable of inducing an IgE-mediated immune response in a subject against a circulating tumor-associated antigen that is not a cell surface antigen. Such IgE monoclonal antibodies are able to direct hypersensitivity reactions and alter antigen processing to cancer (i.e. tumor-associated antigens) while avoiding systemic hypersensitivity reactions that may be harmful to the subject such as systemic anaphylaxis. Without being limited to any particular theory of operability, the inventors have discovered that IgE antibodies in accordance with the invention will target a tumor that is secreting circulating TAAs by two parallel pathways. The first pathway is by mediating bystander antibody-dependent cell-mediated cytotoxicity (ADCC) and also possibly by phagocytosis (ADCP) effects in the tumor microenvironment due to the high local antigen density in the tumor environment. Local concentration gradients in tumor occur from natural accumulation adjacent to tumor cells, aggregates associated with matrix proteins that bind secreted PSA, and also in the case of necrotic or apoptotic tumor, from membrane bound PSA exposed to the extracellular space from the fraction of disrupted cells. All these conditions will facilitate FcεRI mediated local degranulation. It is believed that secretion by the tumor of the TAA into the extracellular space of the tumor microenvironment in the presence of the IgE antibodies of the invention facilitates the cross linking of Fcε receptors (FcεR) to mediate mast cell and basophil degranulation and ADCC by eosinophils, macrophages, monocytes and other effectors thus resulting in tumor site inflammation and local, but not systemic hypersensitivity reactions. With regard to cancer antigens (e.g. circulating TAA) that are not cell surface antigens, it was previously believed that tumor cell killing through an ADCC or CDC mechanism was not expected for antigens not expressed at the cell surface.

The second pathway is by a Th1/Tc1-type immune response or enhanced immune response due to the uptake of immune complexes composed of anti-antigen IgE and circulating tumor-associated antigen by antigen presenting cells. It is believed that due to the expression of FcεR on dendritic cells the immune complexes comprising the tumor-associated antigen and the IgE will be processed to give rise to activated T and B cells. Currently the state of the art teaches that when immune complexes consisting of antigen and polyclonal IgE antibodies or IgE antibodies to a multi-epitopic allergen bind to antigen presenting cells in atopic individuals as well as to mast cells or basophils, the FcεR would be crosslinked, which leads to cellular activation, local cytokine production favoring a Th2 biased immune response, activation of T helper 2 (Th2) cells, and secretion of interleukin (IL)-4 and IL-5. Thus the art expects that the cytokines will subsequently induce Th2 immunity and lead to allergic inflammation including recruitment and activation of eosinophils and other allergic inflammatory cells. Maurer, D., et al., *J. Immunol.*, 161: 2731-2739 (1998) and Maurer D., et al., *J. Immunol.*, 154: 6285-6290 (1995). The art does not address immunity in a circumstance where the antigen is self tumor antigen and not an allergen.

However, the inventors have found that when immune complexes consisting of antigen and monoclonal IgE antibodies to a tumor antigen epitope that is not highly repetitive or that is a non-repetitive epitope are bound by dendritic cells derived from a non atopic patient in an in vitro cell culture system, the dendritic cells express primarily Fc epsilon RII and produce a T cell stimulation to the antigen that has characteristics of a Th1/Tc1 immune response, with prominent induction of IFN-gamma producing CD4 and CD8 antigen specific lymphocytes. Of particular importance is the generation through this mechanism of specific and protective CD8 IFN-gamma positive cytotoxic T-lymphocytes (CTLs) response against the antigen which will cause lysing of tumor cells in the tumor microenvironment or at metastatic sites that express the tumor antigen in context of MHC class I.

Together, these mechanisms can result in an acute inflammation of the tumor microenvironment with subsequent tumor destruction. The presence of dying tumor cells would further allow the effective uptake and presentation of other tumor-associated antigens by antigen presenting cells (APCs), such as dendritic cells resulting in an efficient priming of the adaptive immune response. While potentially very powerful in destroying antigen-associated tumors, administration of IgE antibodies raises the concerns of possible direct systemic immediate hypersensitivity. The approach of the present invention is distinguished in that the IgE antibodies of the invention are monoclonal with single epitope specificity to an epitope that is not highly repetitive, or is a non-repetitive epitope of the tumor-associated antigen. Systemic reactions such as systemic anaphylaxis are generally associated with a polyclonal IgE response, and production of T cell derived mast cell activating factors that permit a local reaction to become systemic. Systemic reactions are associated with the vigorous crosslinking associated with a multi-epitopic polyclonal IgE response. Immune complexes comprising a circulating tumor-associated antigen (TAA) in combination with an antibody of the invention to a non-repetitive epitope of the TAA will be relatively less likely to crosslink FcεR to the level of systemic symptoms when bound to mast cells or granulocytes in circulation than compared to antigen specific polyclonal IgE. Furthermore, it is believed that the therapeutic dosage will be much lower than that associated with IgG classes of antibody therapy against cancer (e.g. trastuzumab (HERCEPTIN®) and rituximab (RITUXAN®)) due to the high affinity of IgE to the FcεR.

A "therapeutic IgE antibody" of the invention (also referred to herein as a "monoclonal IgE antibody of the invention") is a monoclonal antibody that comprises Fc epsilon (ε) constant regions and also comprises variable regions comprising at least one antigen binding region specific for a circulating, tumor-associated antigen (TAA) that is not a cell surface antigen The term "monoclonal IgE antibody of the invention" further encompasses IgE monoclonal antibody derivatives wherein cytokines, chemokines or other immunomodulator proteins are fused to the IgE antibodies of the invention. The term "cancer antigen" as used herein can be any type of cancer antigen known in the art. A preferred cancer antigen of the invention is a circulating tumor-associated antigen (TAA) that is not a cell surface antigen.

Circulating tumor-associated antigens that are not cell surface antigens include any soluble antigen that is detectable in body fluid (e.g. blood serum ascites, saliva or the like), that is of tumor origin and that has been shed, secreted or otherwise released from the tumor, but that is not expressed on the surface of the tumor as an intact protein directly detectable by an IgE monoclonal antibody of the invention. The most well known of such antigens is prostate specific antigen (PSA), however other organ specific antigens produced by organ specific malignancies are posited to exist, but are not associated with popular population screening assays. Such alternative tumor antigens are also subject to this invention.

The terms "monoclonal antibody" or "monoclonal antibodies" as used herein refer to a preparation of antibodies of single molecular composition. A monoclonal antibody composition displays a single binding specificity and affinity for a particular epitope. The monoclonal antibodies of the present invention are preferably chimeric, humanized, or fully human in order to bind human Fc epsilon receptors when the subject host is a human. Humanized and fully human antibodies are also useful in reducing immunogenicity toward the murine components of, for example, a chimeric antibody, when the host subject is human.

The term "chimeric monoclonal antibody" refers to antibodies displaying a single binding specificity which have one or more regions derived from one antibody and one or more regions derived from another antibody. In one embodiment of the invention, the constant regions are derived from human Fc epsilon (ε) (heavy chain) and human kappa or lambda (light chain) constant regions. The variable regions of a chimeric IgE monoclonal antibody of the invention are typically of non-human origin such as from rodents, for example, mouse (murine), rabbit, rat or hamster.

As used herein, "humanized" monoclonal antibodies comprise constant regions are derived from human Fcε (heavy chain) and human kappa or lambda (light chain) constant regions. The variable regions of the antibodies preferably comprise a framework of human origin and antigen binding regions of non-human origin.

Fully human or human-like antibodies may be produced through vaccination of genetically engineered animals such as mouse lines produced at Abgenix Inc. (Thousand Oaks, Calif.) and MedaRex (Princeton, N.J.) which contain the human immunoglobulin genetic repertoire and produce fully human antibodies in response to vaccination. Further, the use of phage display libraries incorporating the coding regions of human variable regions which can be identified and selected in an antigen screening assay to produce a human immunoglobulin variable region binding to a target antigen.

The term "antigen binding region" refers to that portion of an antibody of the invention which contains the amino acid residues that interact with an antigen and confer on the antibody its specificity and affinity for the antigen. The antibody region includes the "framework" amino acid residues necessary to maintain the proper confirmation of the antigen binding residues.

An "antigen" is a molecule or portion of a molecule capable of being bound by an antibody which is additionally capable of inducing an animal to produce antibody capable of binding to an epitope of that antigen. An antigen can have one or more epitopes that are the same or different. In a preferred embodiment, the antibodies of the invention are specific for a single epitope that is not highly repetitive, or a non-repetitive epitope of the antigen. When the epitope is a non-repetitive epitope of the antigen, immune complex formed by an antibody of the invention and the antigen is referred to as "monovalent" in that each antigen molecule may be bound by only one antibody of the invention at any one time. In one embodiment, the antigen is a capable of being bound by an IgE antibody of the invention to form an immune complex that is capable of inducing a specific IgE-mediated immune response to the antigen in a subject capable of mounting such immune response. In one embodiment, the antigen, on its own, may not be capable of stimulating an immune response for any number of reasons, for example, the antigen is a "self" antigen, not normally recognized by the immune system as requiring response or the immune system has otherwise become tolerant to the antigen and does not mount an immune response.

The term "epitope" is meant to refer to that portion of an antigen capable of being recognized by and bound by an antibody at one or more of the antibody's binding regions. Epitopes generally comprise chemically active surface groupings of molecules such as amino acids or sugar side chains and have specific three dimensional structure characteristics as well as specific charge characteristics. An epitope that is not "highly repetitive" means an epitope whose frequency and configuration upon the antigen are such that when an immune complex is formed between the IgE antibody and the antigen, such immune complex does not cause crosslinking of the Fcε receptors on dendritic cells or other relevant antigen presenting cells. The term "non-repetitive epitope" means that only one such epitope is present in the antigen and that the immune complex that is formed between the IgE antibody of the invention and the antigen forms a monovalent immune complex.

An "immune complex" is a complex formed by an antibody and its target antigen. An immune complex may be multimeric or monovalent as described earlier. Methods for raising antibodies, such as murine antibodies to an antigen and determining if a selected antibody binds to a unique antigen epitope are well known in the art.

Screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For preparation of monoclonal antibodies, any technique that provides for the production of antibody molecules by continuous cell lines in culture may be used (see, e.g., Antibodies—A Laboratory Manual, Harlow and Lane, eds., Cold Spring Harbor Laboratory Press: Cold Spring Harbor, N.Y., 1988). These include but are not limited to the hybridoma technique originally developed by Kohler and Milstein (1975, *Nature* 256:495-497), as well as the trioma technique, the human B-cell hybridoma technique (Kozbor et al., 1983, *Immunology Today*, 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. U.S.A.,* 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, *J. Bacteriol.* 159: 870; Neuberger et al., 1984, *Nature* 312:604-608; Takeda et al., 1985, *Nature* 314: 452-454) by splicing the genes from a mouse antibody molecule specific for a polypeptide together with genes from a human antibody molecule of appropriate biological activity can be used; such antibodies are within the scope of this invention.

In a preferred embodiment, the antibody of the invention is specific for a single, non-repetitive epitope of PSA. In one embodiment, the antibody of the invention is specific for the epitope of PSA comprising amino acids 139 to 163 EEFLTPKKLQCVDLHVISNDVCAQV (SEQ ID NO: 1) of PSA. The exact epitope spans from amino acids 137-143 EPEEFLT (SEQ ID NO: 2) of PSA. In one embodiment, the antibody of the invention is capable of binding PSA at the epitope defined at SEQ ID NO: 2. In one embodiment, the antibody of the invention is capable of binding all or any portion of the PSA epitope that extends from amino acids 135 to 163 having the amino acid sequence: SIEPEEFLTPKKLQCVDLHVISNDVCAQV (SEQ ID NO: 3). The amino acid numbering used herein is based on the mature circulating PSA protein that does not include the cleaved 24 amino acid leader sequence.

In a preferred embodiment, the antibody of the invention comprises the variable regions of the light and heavy chain of MAb-AR47.47 and the human kappa or lambda (light chain) and human Fcε (heavy chain) constant regions. MAb-AR47.47 is a monoclonal murine IgG antibody that is specific for the epitope expanding from amino acids 139 to 163 of PSA. Mab-AR47.47 is disclosed in detail in U.S. Pat. No. 6,881,405, incorporated herein by reference. Mab-AR47.47 is produced by a hybridoma that has ATCC Designation Number 1-18-12526. In one embodiment, the IgE monoclonal antibody of the invention is specific for the epitope of PSA to which the monoclonal antibody MAb-AR47.47 also specifically binds.

In one embodiment, antibodies in accordance with the present invention are constructed by genetically fusing the cDNA encoding the variable regions of the light and heavy chain of MAb-AR47.47 to the DNA encoding the human kappa (light chain) and human Fcε (heavy chain) constant regions, respectively. The positive transfectoma identified by enzyme-linked immunosorbent assay (ELISA) and Western Blot, will be cloned for highest productivity and selected for antibody production. As used herein a "transfectoma" includes recombinant eukaryotic host cells expressing the antibody, such as Chinese hamster ovary (CHO) cells and NS/O myeloma cells. Such transfectoma methodology is well known in the art (Morrison, S. (1985) *Science,* 229:1202). Previously published methodology used to generate mouse/human chimeric or humanized antibodies has yielded the successful production of various human chimeric antibodies or antibody fusion proteins (Helguera G, Penichet M L., *Methods Mol. Med.* (2005) 109:347-74).

In general, chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science,* 240:1041-1043); Liu et al. (1987) *PNAS,* 84:3439-3443; Liu et al., 1987, *J. Immunol.,* 139:3521-3526; Sun et al. (1987) *PNAS,* 84:214-218; Nishimura et al., 1987, *Canc. Res.,* 47:999-1005; Wood et al. (1985) *Nature,* 314: 446-449; and Shaw et al., 1988, *J. Natl Cancer Inst.,* 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, *Science,* 229:1202-1207 and by Oi et al., 1986, *BioTechniques,* 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution (U.S. Pat. No. 5,225,539; Jones et al. 1986 *Nature,* 321:552-525;

Verhoeyan et al. 1988 *Science,* 239:1534; and Beidler et al. 1988 *J. Immunol.,* 141:4053-4060).

In one embodiment, the immunogenicity of an IgE monoclonal antibody of the invention is reduced as compared to, for example, the parent antibody from which it was derived, using various strategies. For example, a chimeric IgE monoclonal antibody of the invention comprising human Fcε constant regions and murine variable regions may be rendered less immunogenic to the human subject by genetically engineering humanized antibodies which comprise constant regions that are derived from human Fcε and variable regions that comprise a framework of human origin and antigen binding regions of non-human origin that maintain the same antigen specificity as that of the parent chimeric antibody. Alternatively, fully human or human like antibodies comprising the same antigen specificity as the parent chimeric IgE monoclonal antibodies may also be genetically engineered using known procedures.

Other processes for reducing the immunogenicity of IgE monoclonal antibodies of the invention include, but are not limited to, processes such as DE-IMMUNIZATION™ (Biovation Ltd., Aberdeen, United Kingdom and Merck KgaA, Darmstadt, Germany). This technology is a process that identifies murine epitopes present on murine or chimeric monoclonal antibodies that might cause immunogenicity in humans such as "human anti-mouse antibody" (HAMA) or "human anti-chimeric antibody" (HACA). This process further genetically alters these epitopes to avoid or at least reduce immunogenicity as compared to antibodies that have not been subjected to this process.

Other methods of reducing immunogenicity of monoclonal antibodies (Lazar et al., *Mol Immunol.,* 44, 1986-1998 (2007)) identifies framework and antigen binding region peptides or conformational motifs that may activate T-helper cells resulting in HAMA or HACA responses. Using this method a novel quantitative paradigm is used to determine the "humanness" of murine variable regions and murine regions of low human identity can be substituted for regions of higher human identity thereby reducing immunogenicity of the antibody.

In one embodiment an IgE monoclonal antibody of the invention is genetically fused or chemically conjugated to a protein such as a cytokine, chemokine or other immunomodulator protein. Methods for preparing recombinant antibodies fused to various proteins are described in U.S. Pat. No. 5,650,150. A review of antibody-cytokine fusion proteins is found at Helguera et al, *Clinical Immunology,* 105:233-246 (2002); Helguera and Penichet, *Methods Mol Med.* 109:347-74 (2005); and Ortiz-Sánchez et al, *Expert Opin Biol Ther.* 8(5):609-632 (2008).

In one embodiment, the immunomodulator is a cytokine selected from the group consisting of BDNF, CNTF, EGF, Epo, FGF, Flt3L, G-CSF, GM-CSF, I-309/TCA-3, gamma-IP-10, IFN alpha, IFN beta, IFN gamma, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, LIF, LT, MCP-1 through MCP-3, M-CSF, MIF, MIP-1alpha, MIP-1beta, MIP-2, NGF, NT-3, NT-4, OSM, PBP, PBSF, PGFD, PF-4, RANTES, SCF, TGF alpha, TGF beta, TNF alpha, Tpo and VEGF. Suitable cytokines that are chemokines, can be selected from the group consisting of C10, EMF-1, ENA-78, Eotaxin, GCP-2, HCC-1, 1-309, IL-8, IP-10, Lymphotactin, MCP-1, MCP-2, MCP-3, MGSA, MIG, MIP-1alpha, MIP-1beta, MIP-2, NAP-2, PF4, RANTES, SCM-1 and SDF-1. The cytokine portion of the aforementioned immunomodulator can be the entire cytokine protein amino acid sequence, or a fragment of such fusion protein sufficient to elicit a cytokine-specific biological response.

Preferred immunomodulators or cytokines used to create fusion IgE antibodies of the invention include granulocyte/macrophage-colony stimulating factor (GM-CSF), interleukin-2 (IL-2), interleukin-12 (IL-12), interferon gamma (IFNγ) and interferon alpha (IFNα).

A suitable junction between a cytokine polypeptide chain and an IgE monoclonal antibody of the invention includes a direct polypeptide bond, a junction having a polypeptide linker between the two chains, or other chemical linkage between the chains including the use of biotinylation and the avidin-biotin complex. In one embodiment, the junction is either a direct or polypeptide linker spaced polypeptide linkage. This direct linkage allows for the expression of the immunotherapeutic agent as a single fusion protein, from a host cell transformed with a suitable expression vector encoding for the fusion protein immunotherapeutic agent.

In one embodiment, the IgE monoclonal antibody of the invention may be chemically conjugated to an immunomodulator that is a cytotoxic agent. A suitable cytotoxic agent is one which has a direct cytotoxic effect on the tumor cell, e.g. immunotoxins, radioisotopes, cytotoxic drugs, and the like. Like cytokine immunomodulators described above, cytotoxic peptides can be joined to the IgE monoclonal antibodies to form a fusion protein either directly, or spaced by a linker peptide or chain. Chemical linkage of chemical cytotoxins to the IgE monoclonal antibodies can be made. Radioisotope bearing IgE antibodies chains can also be constructed. IgE monoclonal antibodies of the invention may also be chemically conjugated to other immunomodulators selected from non-protein, protein mimetic or synthetic therapeutic (e.g. small molecules or oligonucleotides) immunomodulators including but not limited to: toll-like receptor agonists, immunostimulatory oligodeoxynucleotides, cytokine blockers, and specific cytokine receptor antagonists.

The invention provides methods for inducing an IgE-mediated immune response against a circulating TAA that is not a cell surface antigen in a subject capable of mounting said immune response comprising administering to the subject an effective amount of an IgE monoclonal antibody that specifically binds a single epitope of a circulating tumor-associated antigen that is not a cell surface antigen, wherein the epitope is not highly repetitive against the tumor such that an IgE-mediated immune response is elicited. As used herein, a "subject capable of mounting (the referenced) immune response" is a subject such as a human patient or other animal subject with functional T-cells, mast cells, eosinophils and dendritic cells with receptor affinity for the administered IgE antibody of the invention as distinguished from non-human animal models, for example, whose immune systems do not contain Fc epsilon receptors capable of binding human IgE permitting generation of functional T-cells, mast cells, eosinophils and dendritic cells in response to the administered antibody.

As used herein the induction of an IgE-mediated immune response includes one or more of the following:

i) Hypersensitivity against the antigen/IgE immune complex particularly in the tumor micro-environment as evidenced by degranulation of mast cells and basophils bound to such immune complex via IgE antibody receptors FcεRI and/or FcεRII and the release of histamine, for example;

ii) Direct targeting of tumor cells via ADCC immune responses, ADCP immune responses or both ADCC and ADCP immune responses against the antigen/IgE immune complex particularly in the tumor micro-environment as evidenced by the stimulation of eosinophils, mast cells, basophils, and other cells to release pro-inflammatory cytokines, proteases and vasoactive lipid mediators (e.g. leukotrienes, prostaglandin D2, and platelet activating factor when bound to the antigen/IgE immune complex via IgE antibody receptors FcεRI and FcεRII;

iii) a cellular response as evidenced in part by the production of T-cells that are specific for the antigen, the antigen/IgE antibody immune complex, or a peptide of the antigen complexed with MHC;

iv) a Th1/Tc1 immune response in response to challenge with the antigen/IgE antibody immune complex as evidenced, for example, by the production of CD8 IFN gamma positive T cells in response to the tumor antigen and tumor;

v) a humoral response as evidenced by production of antibodies against the antigen or the antigen/IgE immune complex.

As used herein an "effective amount" of an IgE monoclonal antibody of the invention is that amount sufficient to recognize and bind the epitope of the circulating TAA that is not a cell surface antigen and induce, elicit, or enhance the referenced immune response in accordance with the invention.

The invention also provides a method for inducing an IgE-mediated immune response against a tumor that is associated with a circulating antigen that is not a cell surface antigen in a subject capable of mounting such a response comprising administering to the subject an effective amount of an IgE monoclonal antibody that specifically binds a single epitope of the circulating antigen wherein the epitope is not highly repetitive or is non-repetitive, and wherein an IgE mediated immune response against the tumor is elicited.

As used herein the induction of an IgE-mediated immune response against a tumor that is associated with a circulating antigen that is not a cell surface antigen, is evidenced, in part, by any one of the following:

i) the inhibition of tumor growth and/or the facilitation of tumor destruction in whole or in part resulting from acute inflammation of the tumor environment and subsequent tumor inhibition/destruction via effector cells bearing human Fc epsilon receptors able to bind—monoclonal IgE antibody and direct ADCC immune responses, ADCP immune responses or both ADCC and ADCP immune responses reactions to the antigen in the micro-environment;

ii) T cell response evidenced by the production of T-cells against the tumor antigen and secondarily additional antigens derived from the tumor and expressed in the context of MHC on the tumor cell resulting in tumor inhibition or tumor lysing; or iii) T cell response against the tumor evidenced by the production of T cells against other antigens associated with tumor cells that have been lysed as above in (ii).

The invention also provides methods of inducing direct IgE-mediated ADCC immune responses, ADCP immune responses, or both ADCC and ADCP immune responses to a circulating TAA that is not a cell surface antigen in a subject capable of mounting such an immune response comprising administering to the subject an effective amount of an IgE monoclonal antibody that specifically binds a single epitope of the circulating antigen wherein the epitope is not highly repetitive or is non-repetitive, and wherein an IgE mediated ADCC immune response and possibly or optionally an ADCP immune response against the antigen is elicited. In a preferred embodiment, the ADCC immune response and possibly or optionally an ADCP immune response is elicited in the microenvironment of a tumor that is secreting the circulating TAA. A local concentration gradient capable of triggering effector cells is the product of secretion, complexation of local antigen with extracellular proteins, and release of membrane associated PSA from apoptotic and necrotic tumor cells present in the tumor cluster In another embodiment the ADCC immune response and possibly or optionally an ADCP immune response is capable of causing the lysing and killing of tumor cells within the tumor microenvironment via bystander effects.

The invention also provides methods for inducing or enhancing a Th1/Tc1 type immune response (particularly CD8 CTL response) to a circulating TAA that is not a cell surface antigen comprising administering to a subject capable of mounting such response, an IgE antibody of the invention that specifically binds a single epitope of a circulating tumor-associated antigen that is not a cell surface antigen, wherein the epitope is not highly repetitive or is non-repetitive. As discussed above, it is known from the allergy literature that polyclonal IgE antibodies to allergen induce a Th2-type immune response. In contrast, is believed that monoclonal IgE antibodies of the invention will primarily produce Th1/Tc1 (e.g. a CD4, CD8 CTL, IFN gamma associated cellular response) in the context of IgE directed to self antigen and also the humoral immune response mediated by B cells. The effect of a primary CD8 CTL response would be to mediate anti-tumor effects with reduced tendency to induce clinically worrisome immediate hypersensitivity in a patient such as systemic anaphylaxis. Additionally or alternatively, the methods of the invention may reduce or eliminate systemic hypersensitivity by reducing or eliminating crosslinking of Fcε receptors which is the cause of mast cell or basophil degranulation.

The invention also provides a method for the treatment of cancer associated with the antigen to which the antibody of the invention is specific, by administering a composition comprising an IgE monoclonal antibody of the invention that specifically binds a single epitope of a circulating, tumor-associated antigen that is not a cell surface antigen, wherein the epitope is not highly repetitive. In one embodiment, the invention provides a method of treating prostate cancer in a subject by administering to the subject a therapeutic IgE monoclonal antibody of the invention that specifically binds a single epitope of PSA wherein the epitope is not highly repetitive.

The present invention also provides pharmaceutical compositions. Such compositions comprise a therapeutically effective amount of an antibody of the invention and a pharmaceutically acceptable carrier. In one preferred embodiment, the pharmaceutical composition comprises a therapeutic IgE monoclonal antibody of the invention that specifically binds a single epitope of PSA wherein the epitope is not highly repetitive in combination with a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of the cancer associated with the antigen to which the antibody of the invention is specific and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For the antibodies of the invention, the dosage administered to a patient is typically 0.001 µg/kg to 1 mg/kg of the patient's body weight. Preferably, the dosage administered to a patient is between 0.01 µg/kg and 0.1 mg/kg of the patient's body weight, more preferably 0.02 µg/kg to 20 µg/kg of the patient's body weight. Generally, the IgE monoclonal antibodies of the invention have a much higher affinity for the Fcε R (as compared to IgG antibodies, for example) and longer half-life within the human body than antibodies from other species. Thus, lower dosages of the antibodies of the invention and less frequent administration is often possible.

Pharmaceutical compositions of the invention also can be administered in combination therapy, i.e. combined with other agents. For example a combination therapy can include a composition of the present invention with at least one anti-tumor agent, efficacy enhancing agent, and/or safety enhancing agent.

The pharmaceutical compositions of the present invention have in vitro and in vivo diagnostic and therapeutic utilities. For example, these molecules can be administered to cells in culture, e.g., in vitro or ex vivo, or in a subject, e.g., in vivo, to treat cancer. As used herein, the term "subject" is intended to include human and non-human animals. A preferred subject is a human patient with cancer. As used herein the terms "treat" "treating" and "treatment" of cancer includes: inhibiting the onset of cancer in a patient; eliminating or reducing tumor burden in a patient; prolonging survival in a cancer patient; prolonging the remission period in a cancer patient following initial treatment with chemotherapy and/or surgery; and/or prolonging any period between cancer remission and cancer relapse in a patient.

As used herein, "administering" refers to any action that results in exposing or contacting a composition containing an antibody of the invention with a pre-determined cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells.

In accordance with a method of the invention compositions comprising the IgE monoclonal antibody of the invention may be administered to the patient by any immunologically suitable route. For example, the antibody may be introduced into the patient by an intravenous, subcutaneous, intraperitoneal, intrathecal, intravesical, intradermal, intramuscular, or intralymphatic routes. The composition may be in solution, tablet, aerosol, or multi-phase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The invention should not be limited to any particular method of introducing the binding agent into the patient.

When used for therapy for the treatment of cancer, the antibodies of the invention are administered to the patient in therapeutically effective amounts (i.e. amounts effective to eliminate or reduce the patient's tumor burden or otherwise ameliorate the symptoms of cancer in the patient). The antibodies of the invention and the pharmaceutical compositions containing them will normally be administered parenterally, when possible, at the target cell site, or intravenously.

In another embodiment, the IgE antibodies of the invention can be co-administered with a therapeutic agent, e.g., a chemotherapeutic agent, an immunosuppressive agent (e.g. Rituximab), an anti-inflammatory agent, or can be co-administered with other known therapies, such as physical therapies, e.g., radiation therapy, hyperthermia, transplantation (e.g., bone marrow transplantation), surgery, sunlight, or phototherapy. Such therapeutic agents include, among others, antineoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/m$^2$ dose once every four weeks and adriamycin is intravenously administered as a 60-75 mg/m² dose once every 21 days.

Pharmaceutical compositions of the present invention can include one or more further chemotherapeutic agents selected from the group consisting of nitrogen mustards (e.g., cyclophosphamide and ifosfamide), aziridines (e.g., thiotepa), alkyl sulfonates (e.g., busulfan), nitrosoureas (e.g., carmustine and streptozocin), platinum complexes (e.g., carboplatin and cisplatin), non-classical alkylating agents (e.g., dacarbazine and temozolamide), folate analogs (e.g., methotrexate), purine analogs (e.g., fludarabine and mercaptopurine), adenosine analogs (e.g., cladribine and pentostatin), pyrimidine analogs (e.g., fluorouracil (alone or in combination with leucovorin) and gemcitabine), substituted ureas (e.g., hydroxyurea), antitumor antibiotics (e.g., bleomycin and doxorubicin), epipodophyllotoxins (e.g., etoposide and teniposide), microtubule agents (e.g., docetaxel and paclitaxel), camptothecin analogs (e.g., irinotecan and topotecan), enzymes (e.g., asparaginase), cytokines (e.g., interleukin-2 and interferon-.alpha.), monoclonal antibodies (e.g., trastuzumab and bevacizumab), recombinant toxins and immunotoxins (e.g., recombinant cholera toxin-B and TP-38), cancer gene therapies, physical therapies (e.g., hyperthermia, radiation therapy, and surgery) and cancer vaccines (e.g., vaccine against telomerase).

The present invention is further illustrated by the following non-limiting examples.

Example 1

Preliminary Study Involving the Construction of an IgG1 and IgG3 Chimeric Antibody with Human Constant Regions The methodology used to generate mouse/human chimeric or humanized antibodies that has yielded the successful production of various human chimeric antibodies or antibody fusion proteins is described (Helguera, G. and Penichet, M L, Methods Mol. Med., 109: 347-374 (2005)). A chimeric version of MAb-AR47.47 is described in U.S. Pat. No. 6,881,405. Briefly, the plasmid construction originated from the RNA of the murine hybridoma AR47.47, extracted using the RNeasy Mini Kit (Qiagen, Valencia, Calif.). cDNA was then prepared using the SuperScript III First-Strand synthesis System for RT-PCR (Invitrogen, Carlsbad, Calif.). Both the heavy and light chain variable regions were amplified by PCR and cloned into the PCR-BLUNT II-TOPO® vector using the ZERO BLUNT® TOPO® PCR Cloning Kit (Invitrogen). After sequence confirmation, the murine heavy chain variable region was then subcloned into two expression vectors, containing either the human IgG1 or human IgG3 constant regions. Both heavy chain expression vectors contain the sequences for the $C_H1$, hinge, $C_H2$, and $C_H3$ domains under the control of a CMV promoter. The murine heavy variable region was cloned in frame with the human $C_H1$ domain. The murine variable light chain was subcloned into a single expression vector containing the human kappa constant region under the control of a CMV promoter.

Expression in murine myeloma cells: Anti-PSA light chain producers were first developed by electroporation of either Sp2/0Ag14 or P3X63Ag8.653 murine myeloma cells with the light chain expression vector. The best light chain producer was identified by ELISA and transfected with both the heavy and light chain expression vectors (IgG3 and kappa expression vectors or IgG1 and kappa expression vectors). It is our experience that production of the light chain is a major limiting factor for optimal production and secretion of recombinant antibodies. For this reason, cotransfection is performed in order to maximize the production of antibody by the myeloma cells. The clones were screened by ELISA for the production of either IgG1 or IgG3 antibodies.

Testing: Secretion of human antibody was screened by ELISA for human kappa and human gamma chain. The best producers were selected based on the ELISA signal and colony size. The smallest colonies with the highest signal were chosen and expanded for further characterization. Antibodies secreted from various clones were tested for proper assembly, secretion, and molecular weight of the recombinant antibodies using $^{35}$S-labeling and immunoprecipitation. Correctly assembled clones with high productivity were then tested for binding to PSA by ELISA.

All three expression vectors were successfully constructed and transfected into murine myeloma cells. Both the anti-PSA IgG3 and IgG1 antibodies were properly assembled and secreted as evidenced by $^{35}$S-labeling and immunoprecipitation. In each clone, the full antibody complex shows the expected molecular weight (approximately 170 kDa for IgG3). As an example of reducing conditions, the immunoprecipitation results of five clones of anti-PSA IgG1. All five clones show the presence of both the heavy chain (approximately 50 kDa) and the light chain (approximately 25 kDa). Antigen binding studies were performed using the supernatants of transfectomas. Both anti-PSA IgG3 and IgG1 demonstrate the ability to bind a PSA peptide that is recognized by the murine AR47.47 murine IgG1 antibody. Direct supernatants as well as supernatants from a non-targeting, negative control mouse/human chimeric antibody were tested. Dilutions of the supernatants were also tested to demonstrate dose dependent binding of the antibody to the antigen. The supernatant of anti-PSA IgG3 demonstrates greater signal than the IgG1, which is due to higher productivity of the IgG3 clones compared with the IgG1 counterparts. Further studies with purified antibodies need to be conducted to directly compare antibody-binding capabilities.

Example 2

Construction of the Human/Mouse Chimeric Anti-PSA IgE Antibody

A cell line that produces mouse/human chimeric light chain (kappa) with the variable regions of the AR47.47 light chain has already been obtained by transfecting the murine myeloma cell lines P3X63Ag8.653 and Sp2/0-Ag14 by electroporation with the mammalian expression vector during construction of the mouse/human chimeric IgG1 or IgG3 AR47.47 as discussed in Example 1.

The DNA encoding the variable light (VL) and heavy (VH) chain domains of the AR47.47 antibody have been sequenced and cloned already for the generation of the chimeric AR47.47 IgG1 and IgG3. The variable heavy chain region was subcloned from the chimeric anti-PSA IgG1 vector and cloned into a human IgE expression vector (Chan et al, Molecular Immunology 37 (2000) 241-252) so that the variable region is in frame with the CH1 domain. This heavy chain was then co-transfected into the PSA light chain producer described above.

IgE antibody secreting clones were tested for presence of heavy (epsilon chain) and light chain (kappa chain) by ELISA. The best producers will be selected based on the ELISA signal and colony size. The smallest colonies with the highest signal will be chosen and expanded for further characterization. Antibodies secreted from various clones will be tested for proper assembly, secretion, and molecular weight of the recombinant antibodies using $^{35}$S-labeling and immunoprecipitation. Correctly assembled clones with high productivity will then tested for binding to PSA by ELISA as described in Example 1. The best clones will be further cloned three times and adapted to protein-free media (Hybridoma-SFM, Invitrogen; or HYQ® SFM4MAB™, Hyclone), and grown in roller bottles for production of antibody for Further preclinical study. The antibody will be purified via diafiltration (50 kDa cut-off) and immunoaffinity chromatography on a monoclonal anti-hIgE-Fc MAb (HP6029, HP6061) coupled to HiTrap columns (GE Healthcare).

Example 3

In Vitro Biochemical and Biological Characterization of the Human/Mouse Anti-PSA IgE Binding to PSA antigen: The anti-PSA IgE was assessed for initial PSA binding by ELISA. Microwell Maxi-Sorp plates are coated with PSA (1.5 ug/ml in PBS) and incubated at 4° C. overnight. After washing plates are blocked with 3% BSA/PBS for 30-60 minutes at RT. Samples containing anti-PSA IgE are added in serial dilutions (2 ug/ml, 1 ug/ml, 0.5 ug/ml, 0.25 ug/ml 0.125 ug/ml 0.0625 ug/ml, 0.31 ug/ml) and incubated for 2 hr at RT. The presence of anti-PSA specific IgE Abs is detected by biotinylated goat anti-Human IgE (1:2000 dilution, KPL) followed by Strepavidin-HRP (1:10,000) added separately and incubated for 30-60 min each. The assay is developed with TMB and the reaction is terminated with stop solution ($H_2SO_4$). Absorbance is measured at 405 nm (FIG. 1).

In future studies, a transfectoma secreting anti-DNS IgE and anti-DNS IgG1 (Chan, L A, et al., *Mol. Immunol.*, 37: 241-252 (2000)) will be used as negative controls for specificity. The ELISA is developed for detection of murine and human IgGs and will be adapted for the chimeric IgE by optimizing a human IgE-specific secondary antibody (Sigma-Aldrich). Binding to cells can also be demonstrated by using intracellular staining by flow cytometry or by a cell-based ELISA with confluent layers of LNCaP cells (ATCC), or PSA- and neo-transfected CT26 or P818 cell lines, for example. The cells will be fixed and permeabilized, then blocked and incubated with the anti-PSA IgE as well as anti-PSA IgG and non-specific IgE controls. Bound antibody will be traced with anti-human IgE-HRP and TMB substrate. Specific binding can further be demonstrated by western blots of LNCaP or CT26.PSA lysates in comparison to cell lines not expressing PSA (NIH:OVCAR-3, CT26.neo) as described in Example 1.

Figure 3:
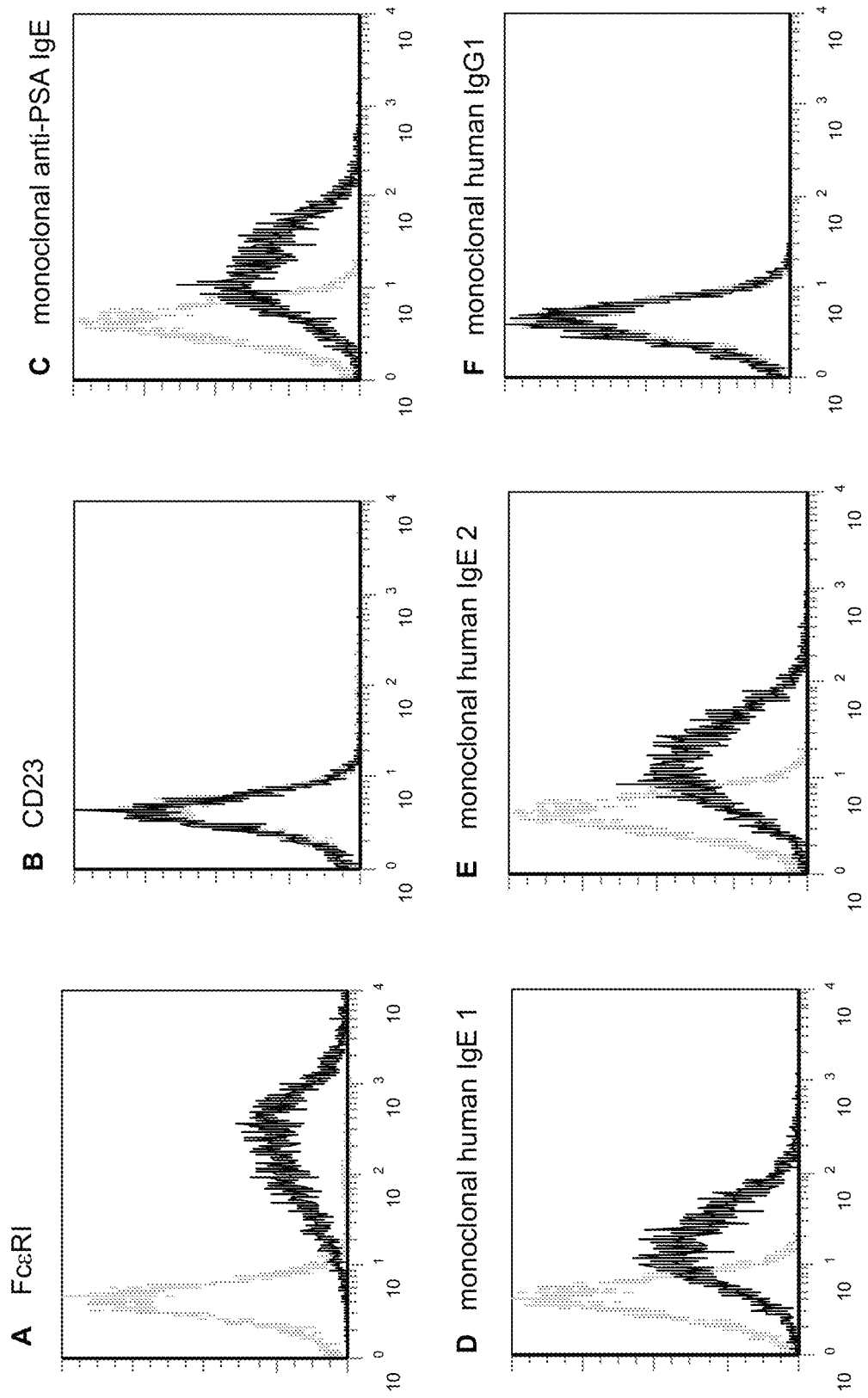
FIGS. 3A-F are read outs from flow cytometric analysis depicting the binding of purified fluorescently labeled anti-PSA IgE to FcεR1α on the surface of CHO-3D10 cells using flow cytometric analysis (FIG. 3C) and comparing to other anti-antigen IgE monoclonal antibodies (FIGS. 3D and 3E) as well as human IgG1 antibody as a negative control (FIG. 3F).

Binding to Fc epsilon receptors: Binding of anti-PSA IgE to the human high-affinity IgE receptor FcεRI was confirmed using the CHO3D10, a human FcεRI alpha chain transfected CHO cell line that binds human Fc epsilon and that has been used by other researchers to study the binding of human IgE (Chan, L A, et al., *Mol. Immunol.*, 37: 241-252 (2000)). As controls (in parallel) the binding of the murine IgG1 and the chimeric human IgG1 and IgG3 were tested. FIG. 3A-F shows binding of purified PSA IgE to FcεR1α on the surface of CHO-3D10 cells using flow cytometric analysis. CHO-3D10 cells express FcεRI, but not FcεRII (CD23) as demonstrated by flow cytometry (FIG. 3A and FIG. 3B). FIG. 3C shows binding of monoclonal anti-PSA IgE to CHO-3D10 cells as detected by a fluorescently labeled anti-IgE Ab and flow cytometric analysis. The anti-PSA IgE binding is similar to other human monoclonal anti-antigen IgE Abs (FIG. 3D and FIG. 3E). The binding is IgE specific since monoclonal human IgG1 binding can not be detected (FIG. 3F).

In future studies, further cell types to be investigated include the cell line HMC-1 that expresses FcεRII but not FcεRI, the lymphoblastoid cell line RPMI 8866 or IM9, which are known to express FcεRII at high density (Mayumi, M., et al., *Clin. Exp. Immunol.*, 71: 202-206 (1988)), the FcεRII-negative human B-lymphoblastoid cell line Daudi (all from ATCC), and isolated human monocytes, immature and matured monocyte-derived Dendritic cells (Berlyn, K A, et al., *Clin. Immunol.*, 101: 276-283 (2001)). CHO cells and anti-DNS IgE and IgG will be used as further negative controls. Binding will be analyzed by flow cytometry using FITC-labeled anti-human IgE and anti-human IgG reagents.

Discrimination of involved receptors on human dendritic cells will be performed by inhibition with fluorescently labeled, commercially available antibodies to CD23 (FcεRII, clone D3.6, Biolegend) and FcεRI. The humanized monoclonal IgG antibody omalizumab (XOLAIR®, Genentech), binding to the receptor-binding region of IgE Fc, can also be used to assess Fcε receptor binding. Its affinity for IgE is extremely high, $1.5 \times 10^{10}$ $M^{-1}$; and this affinity is just high enough to enable it to compete and block soluble IgE binding to FcεRI at high concentrations. Therefore, the concentration-dependence of the inhibition of the anti-PSA IgE will be indicative of the receptors involved.

IgE-mediated antigen uptake, trafficking, and presentation in dendritic cells: The inventors have established the methodology to study the uptake, trafficking, and presentation of PSA complexed with murine and chimeric anti-PSA IgG in human monocyte-derived dendritic cells (Berlyn, K A, et al., *Clin. Immunol.*, 101: 276-283 (2001)) as well as in a HER2/neu system (la Cruz, J S, et al., *Mol. Immunol.*, 43: 667-676 (2006)), and this same technology will be used to study anti-PSA PSA IgE complexed with PSA. Analysis of protein uptake and trafficking in dendritic cells will be conducted by incubating the cells with PSA, labeled with Alexafluor 488 (green fluorochrome) and complexed with anti-PSA IgE or anti-PSA IgG at different concentrations, and over time at 37° C. in tissue culture. Cells will also be incubated in parallel with antigen alone, or combined with anti-DNS IgE or IgG (isotype-matched negative controls). Cells will then be harvested and analyzed for uptake of fluorescent PSA using flow cytometry. For antigen trafficking studies, the cells will be fixed after antigen uptake, permeabilized, and treated with biotinylated rat monoclonal anti-mouse CD71 (anti-murine transferrin receptor, an early endosome marker), biotinylated monoclonal rat anti-mouse CD107a (anti-murine LAMP-1, a lysosome marker) or rabbit polyclonal anti-H2-DM (H2-DM the murine equivalent of human HLA-DM serves as a marker for MHC class II), followed by streptavidin-Alexafluor 568 (red fluorochrome). Antigen uptake and colocalization will then be analyzed by confocal microscopy (la Cruz, J S, et al., *Mol. Immunol.*, 43: 667-676 (2006)). Antigens internalized through endocytosis in APCs traffic through several vesicular compartments such as lysosome and H2-DM that leads to MHC class II antigen presentation. However, dendritic cells that have developed a membrane transport pathway of antigen delivery to the cytosol can also access the cytosolic antigen-processing machinery for MHC class I presentation (Rafiq, K., et al., *J. Clin. Invest.*, 110: 71-79 (2002) and Rodriguez, A., et al., *Nat. Cell Biol.*, 1: 362-368 (1999)). If MHC class I or II restricted T cell lines are not available that are specific for human PSA, the ability of human dendritic cells to present the antigen will be studied using an in vitro antigen presentation assay. Briefly, human dendritic cells will be generated from monocytes (negative magnetic cell isolation kit) with IL-4 and GM-CSF, and incubated with PSA, anti-PSA IgE or immune complexes of PSA and anti-PSA IgE on Day 6.

Anti-PSA IgG alone and as immune complex as well as mock-loaded dendritic cells will serve as controls. Dendritic cells will be matured with LPS or TNF-α/IFN-α for 24 h, washed, and incubated with isolated autologous T cells for 1 week. T cells will be restimulated with freshly prepared and loaded dendritic cells for 3 weekly rounds. Two to 4 h after the final stimulation, cells will be incubated with Brefeldin-A, and harvested 18 h later for intracellular cytokine staining T cells will be incubated with anti-CD3-FITC and anti-CD8-PE/Cy5, washed, permeabilized and then split into groups for staining with anti-IFN-γ-PE, and anti-IL-4-PE or anti-IL-5-PE. The cells will be analyzed by flow cytometry and the percentage of CD8+/cytokine+ as well as CD8-(assuming CD4+)/cytokine+ cells calculated. Predominance of IFN-γ production will indicate induction of a Th1-type response, whereas production of IL-4 or IL-5 is indicative of Th2-type and allergic responses.

Example 4

Assessment of Direct Anti-Tumor Effector Mechanisms

A. ADCC assays: Since human monocytes, macrophages, and eosinophils have been demonstrated to be critical mediators of chimeric IgE anti-tumor ADCC in vitro and in vivo (Karagiannis, S N, et al., *Eur. J. Immunol.*, 33: 1030-1040 (2003), Jensen-Jarolim E, et al., *Allergy*, 63:1255-66 (2008)), tests of the ability of these cells to elicit a cytotoxic effect in LNCaP models will be conducted using a Calcein AM release assay. The Calcein AM release assay is performed equivalently to a $^{51}$Cr release assay, but using fluorescently labeled tumor cells (Invitrogen). Eosinophils will be isolated to >95% purity by Percoll gradient centrifugation (density 1.082 g/ml) (GE Healthcare) followed by immunomagnetic separation with anti-CD 16-coated immunomagnetic beads as described (Kayaba, J I 2001), and used for assays immediately. Monocytes will be isolated using a magnetic negative monocyte isolation kit (Stemcell Technologies). Macrophages will be generated from frozen human PBMC according to standard methods (Gersuk, G, et al., *J. of Immunol Methods*, 299:99-106 (2005)). Briefly, isolated PBMC will be washed 3× with PBS/EDTA and then resuspended in a 2×10$^6$ cells/ml in media (IMDM supplemented with 10% human AB serum, glutamine and pen/strep). Monocytes are isolated by adherence to Falcon PRIMARIA™ coated 24 well tissue culture plates. Cells are allowed to attach to plate for 3 h at 37° C. and non-adherent cells are removed by shaking the plate (3000 rpm for 2 min) and washing cells 2× with PBS/EDTA. The remaining adherent cells are resuspended in 1.5 ml of complete media containing an addition 10% autologous human serum and 40 ng/ml rhM-CSF (R&D systems). Cells are grown for 7-10 days and media is changed on days 4 and 7. In order to assess a bystander effect to a target antigen that is not expressed on the tumor cell surface, but that is secreted into the tumor microenvironment, a 3D culture system may be required for the tumor cells. Multicellular tumor spheroids are prepared using ALGIMATRIX™ 3D culture system (Invitrogen) following manufacturer's instructions. Briefly, multicellular spheroids are generated by seeding 2.5×10$^4$ cells in 30 μl into the middle of a dry sponge followed by culturing for 5-10 days. Viable spheroids can be isolated by dissolving the AlgiMatrix 3D Culture System and used in an ADCC assay with ALAMAR BLUE™ to assess cell viability.

B. Antigen-mediated mast cell degranulation: Mast cell granule release assays will be performed using the rat basophilic leukemia cell line RBL-sx38, which expresses human FcεRI α subunit and endogenous rat FcεRI α, β, and γ subunits. Approximately 10$^6$ RBL-sx38 cells will be incubated in the presence of varying concentrations of anti-PSA IgE complexed with different amounts of PSA. Anti-DNS IgE complexed with DNS-BSA will be used as a positive control. Antibodies without antigen as controls will also be used. The incubations will be done in 1 h at 37° C. Granule release will then be assessed by measurement of the β-hexosaminidase present in the RBL-sx38 cell lysate vs. supernatant fractions (Chan, L A, et al., *Mol. Immunol.*, 37: 241-252 (2000) and Karagiannis, S N, et al., *Eur. J. Immunol.*, 33: 1030-1040 (2003)) or release of histamine as described. Briefly, supernatants from triplicate cell samples will be separated from the corresponding pellets by centrifugation of the samples 30 min after activation. The pellets will be disrupted by three rounds of freeze thawing followed by sonication. The histamine content of the acylated samples will be quantitated with a commercial ELISA (ICN) according to the manufacturer's protocol and the percentage of histamine released relative to histamine in the pellet determined (Ochi, H., et al., *Proc. Natl. Acad. Sci. U.S.A.*, 97: 10509-10513 (2000)). Alternatively, human mast cells purified and generated from human cord blood over 6 weeks of culture in the presence of recombinant stem cell factor (SCF), IL-6, and IL-10 (c-kit+, CD13+, low-level FcεIα, uniform toluidine blue metachromasia) as described by the group of Dr. J. Boyce (Ochi, H., et al., *J. Exp. Med.*, 190: 267-280 (1999)), will be used. Human mast cells can also be derived from peripheral blood CD34$^+$ cells from healthy adult volunteers using magnetic beads (Stemcell Technologies) and culture in StemPro-34 medium (Invitrogen) containing 20% charcoal-filtered FCS, SCF (100 ng/ml), GM-CSF (10 pg/ml), and 4% conditioned medium from an immortalized B cell line over 4 weeks (Jiang, Y., et al., *J. Immunol.*, 177: 2755-2759 (2006)).

C. Local Accumulation of PSA Around PSA Tumor Cells:

A 3-D culture system was developed using PSA- and neo-transfected CT26 tumor cells (J. Frelinger) by creating multicellular spheroids grown in selective media (RPMI-1640, supplemented with 10% FBS, Pen/Strep, glutamine, and G418) and transferring them into a collagen matrix. Briefly, the multicellular spheroids were generated using the hanging droplet method with a drop size of 20 μl, which seeds 2.5-5× 10$^4$ cells in each spheroid. Cell solutions were pipetted onto the inside of a 96-well plate cover, placed over a medium-filled plate, and incubated (5% CO$_2$, 37° C.) for 5 days. The extracellular matrix (ECM) consisting of PureCol (3 mg/ml, Advanced Biomatrix) and 10× RPM1 (9:1) was prepared and neutralized with 0.1 N NaOH to a pH of 7.2-7.6. The ECM solution (75 μl) is pipetted into a sterile 96-well plate and the multicellular spheroids were pipetted into this collagen gel and put in the incubator for 4-6 hours (hr). Once the gel solidified, 75 μl of media was pipetted on top of the collagen to allow diffusion of nutrients into the ECM. Microspheroids were then kept in a sterile incubator until ready for use (from 1-6 days) and media was changed every 2 days. To determine the local accumulation of PSA around the hanging drop cultures and the collagen containing microspheroids, an anti-PSA ELISA was performed. Briefly, ELISA plates were coated with goat anti-PSA Ab (5 ug/ml) overnight at 4° C. The next day, the plates were washed and blocked with 3% FBS in PBS for 1 hr at room temperature (RT). After washing, samples were added (5 hanging drops containing 5×10$^4$ cells cultured for four days, or 4 wells of collagen, media, and microspheres that had been seeded with hanging drops of 2.5 or 5×10⁴ cells cultured for 5 days). Samples were incubated for 2 hr at RT. Plates were again washed and AR47.47 (mouse anti-PSA, 5 µg/ml) was added to each well and incubated for 1 hr at RT. AR47.47 was detected using an anti-mouse HRP conjugated Ab that was added to each well at a 1:8000 dilution and incubated at RT for 1 hr. After washing, developing solution (TMB) was added and the reaction was terminated with stop solution (H$_2$SO$_4$). Absorbance was measured at 450 nm on a spectrophotometer.

Figure 2:
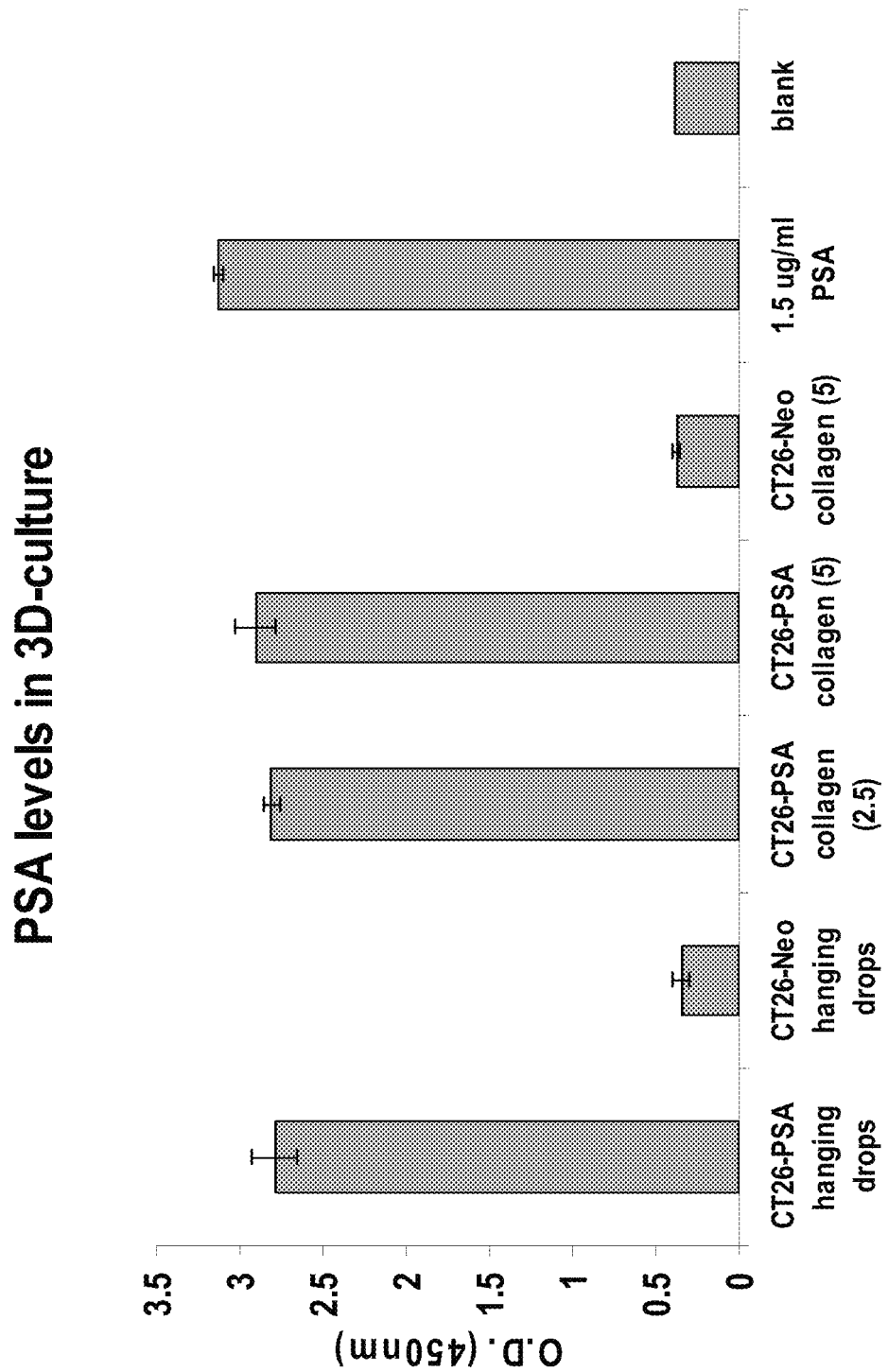
FIG. 2: Demonstration of Local Accumulation of PSA in a tumor cell 3D Collagen cluster. A bar graph plots the signal of intensity to detect PSA using a goat anti PSA ELISA (coated overnight at 5 ug/mL). Spheroid microcultures of CT-26-PSA transfectoma or CT-26-NEO control tumor cells lines are grown as hanging drops of 20 ul and pipetted into a Purecoll (Advanced Biomatrix) 3 mg/ml collagen extracellular matrix preparation and grown for 72 hours. After washing, samples were added (5 hanging drops containing $5 \times 10^4$ cells cultured for four days, or 4 wells of collagen, media, and microspheres that had been seeded with hanging drops of 2.5 or $5 \times 10^4$ cells cultured for 5 days). Samples were incubated for 2 hr at RT. Plates were again washed and AR47.47 (mouse anti-PSA, 5 µg/ml) was added to each well and incubated for 1 hr at RT. AR47.47 was detected using an anti-mouse HRP conjugated Ab that was added to each well at a 1:8000 dilution and incubated at RT for 1 hr. After washing, developing solution (TMB) was added and the reaction was terminated with stop solution ($H_2SO_4$). Absorbance was measured at 450 nm on a spectrophotometer.

PSA is clearly produced and detectible in association with the CT-26 PSA microspheroids but not in a CT-26 control cell line. The positive control is human PSA coated at a concentration of 1.5 µg ml to the control well (FIG. 2).

D. Passive cutaneous anaphylaxis: Passive cutaneous anaphylaxis is performed in transgenic mice expressing the human FcεRIα. Transgenic mice are shaved and injected intradermally in different regions of the dorsal side with 50 µl of 6 mg/ml histamine base (HollisterStier, Spokane, Wash.), 1 µg anti-PSA IgE, CT26-PSA or CT26-Neo microspheroid alone, 2 µg of crosslinker anti-human kappa antibody alone, 1 µg anti-PSA IgE plus CT26-PSA or CT26-Neo microspheroid, or 1 µg anti-PSA IgE crosslinked with 2 µg of an anti-human kappa antibody. After 15 min, 1% Evans Blue in 250 µl saline was injected i.v. Mice are sacrificed 20 min later, and local cutaneous anaphylaxis was assessed visually by the blue leakage in the area surrounding the injection.

E. In vivo anti-tumor effects using anti-PSA IgE: To study the ability of In Vitro primed dentritic cells obtained from our transgenic FcεR1 receptor humanized mice to stimulate the anti-tumor response in vivo, the dentritic cells will be inoculated (s.c.) into the human PSA transgenic mice. This study is possible since the genetic background of both transgenic models is the same (BALB/c). Dentritic cells vaccinated mice will be challenged sc or iv with a lethal dose of human PSA transgenic syngeneic tumors (ie CT26-PSA). The anti-tumor activity will further be studied in mice that are human IgE, human FcεR and human PSA triple transgenic. These mice are tolerant to human PSA and human IgE and allow the growth of syngeneic human PSA expressing tumor cells while being responsive to the human IgE. These mice would be injected s.c. with 0.5-1× 10⁶ PSA expressing tumor cells (i.e. CT26-PSA) to induce tumor formation. Treatment with anti-PSA IgE prior to and subsequent to tumor cell implantation with and with out coordinated co-administration of selected cytotoxic agents such as cyclophosphamide would be used to evaluate the ability of the anti-PSA IgE to limit tumor formation/growth.

Discussion: The anti-PSA IgE antibody of the invention, takes advantage of the expression of PSA in over 90% of prostate cancers; however, the targeted antigen is secreted and not a trans-membrane tumor cell surface. Therefore, mediation of ADCC and ADCP is not expected toward isolated tumor cells. However, it believed that high concentrations of PSA in the extracellular tumor matrix as is discussed above in Example 4C is sufficient to trigger ADCC mediated by eosinophils, monocytes, or macrophages or to degranulate mast cells and basophils locally. However, due to the high affinity of the FcεR and the high density of the receptor on mast cells and eosinophils, we expect that these cells extravasate into the tumor highly loaded with anti-PSA (slow dissociation rate) and will crosslink their receptors when contacting multiple PSA molecules in close proximity, like in the tumor stroma. While the monoclonal IgE is expected to be effective, the role of cross-linking by polyclonal anti-PSA IgG can also be investigated. Furthermore, if the anti-PSA IgE/PSA immune complexes are processed to activate a Th2-type response to PSA, then such polyclonal anti-PSA IgG would be generated in vivo. The anti-PSA antibody with human Fc epsilon constant regions is not expected to mediate direct acute immediate hypersensitivity reactions (via systemic mast cell and basophil degranulation) for the very reason that the antigen is not expressed on the surface of cells and the antibody is targeting a single epitope of PSA; and therefore, only generating monovalentimmune complexes. The inventors believe that this approach should permit safe monoclonal IgE infusion. If PSA-anti-PSA IgE immune complex would trigger Th1-type and CTL responses to PSA, then those effector cells would be able to lyse PSA-expressing tumor cells via a MHC class I and/or II restricted pathway. Either way, this novel IgE approach is expected to target the neoplastic cells with sufficient capacity to orchestrate an anti-tumor immune response. Antibodies against the remaining murine epitopes on the chimeric anti-PSA IgE may induce unwanted cross-linking of the PSA-anti-PSA IgE complexes. Such human anti-chimeric antibodies (HACA), cross-linking IgE on mast cells and granulocytes may induce early and late-phase activation, and thus, may pose a risk for immediate hypersensitivity reactions. Thus, it may be necessary and is possible to fully humanize the anti-PSA IgE according to well known procedures if necessary.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It will also be understood that none of the embodiments described herein are mutually exclusive and may be combined in various ways without departing from the scope of the invention encompassed by the appended claims.

What is claimed is:

1. An IgE monoclonal antibody that specifically binds an epitope of prostate-specific antigen (PSA), wherein the epitope is not highly repetitive.

2. The antibody of claim 1, wherein the monoclonal antibody is a chimeric monoclonal antibody or a humanized monoclonal antibody.

3. The antibody of claim 1 having a constant region that is of human origin.

4. The antibody of claim 1 having variable regions that are of human origin, non-human origin or any combination thereof.

5. The antibody of claim 1, wherein the epitope is a non-repetitive epitope.

6. The antibody of claim 1, wherein said antibody is capable of eliciting an IgE-mediated immune response in a mammal.

7. The antibody of claim 1, which binds to the epitope of PSA defined by amino acids EEFLTPKKLQCVDLHVISNDVCAQV (SEQ ID NO: 1) of PSA.

8. The antibody of claim 1, which binds to the epitope of PSA defined by amino acids SIEPEEFLTPKKLQCVDLHVISNDVCAQV (SEQ ID NO: 3) of PSA or any portion thereof.

9. The antibody of claim 1, wherein the antibody is a chimeric monoclonal antibody, or a fully humanized monoclonal antibody.

10. The antibody of claim 1, which is genetically fused or chemically conjugated to a protein immunomodulator.

11. A method for inducing an IgE-mediated immune response against a prostate-specific antigen (PSA) in a subject capable of mounting said immune response comprising administering to the subject the antibody of claim 1 in an amount effective to induce an IgE-mediated immune response in the mammal.

12. The method of claim 11, wherein the IgE-mediated immune response is induced in the mammal in the absence of systemic hypersensitivity reactions in the subject.

13. The method of claim 11, wherein the IgE-mediated immune response induced in the subject is capable of inhibiting the progression of a tumor secreting the antigen.

14. The method of claim 11, wherein the IgE-mediated immune response induced in the subject against PSA is capable of inhibiting tumor growth or causing tumor destruction of a tumor secreting PSA.

15. A method of inducing a direct ADCC immune response, a direct ADCP immune response, or both, to prostate-specific antigen (PSA) in a subject capable of mounting such a response comprising administering to the subject an effective amount of an IgE monoclonal antibody that specifically binds an epitope of PSA wherein the epitope is not highly repetitive or is non-repetitive, and wherein a direct IgE mediated ADCC or ADCP immune response against PSA is elicited.

16. The method of claim 15, wherein the direct ADCC or ADCP immune response is elicited in the microenvironment of a tumor that is secreting PSA.

17. The method of claim 15, wherein the direct ADCC or ADCP immune response is induced in the absence of systemic hypersensitivity reactions in the subject.

18. A method of treating prostate cancer in a subject comprising administering to the subject a therapeutically effective amount of the IgE monoclonal antibody of claim 1.

* * * * *

SEQUENCE LISTING

<160> NUMBER OF SEQ ID NOS: 3

<210> SEQ ID NO 1
<211> LENGTH: 25
<212> TYPE: PRT
<213> ORGANISM: Homo Sapiens

```
<400> SEQUENCE: 1

Glu Glu Phe Leu Thr Pro Lys Lys Leu Gln Cys Val Asp Leu His Val
 1               5                  10                  15

Ile Ser Asn Asp Val Cys Ala Gln Val
            20                  25

<210> SEQ ID NO 2
<211> LENGTH: 7
<212> TYPE: PRT
<213> ORGANISM: Homo Sapiens

<400> SEQUENCE: 2

Glu Pro Glu Glu Phe Leu Thr
 1               5

<210> SEQ ID NO 3
<211> LENGTH: 29
<212> TYPE: PRT
<213> ORGANISM: Homo Sapiens

<400> SEQUENCE: 3

Ser Ile Glu Pro Glu Glu Phe Leu Thr Pro Lys Lys Leu Gln Cys Val
 1               5                  10                  15

Asp Leu His Val Ile Ser Asn Asp Val Cys Ala Gln Val
            20                  25
```